(12) United States Patent
Clavelle et al.

(10) Patent No.: US 10,000,706 B2
(45) Date of Patent: *Jun. 19, 2018

(54) SERPENTINE FLUID REACTOR COMPONENTS

(71) Applicant: NOVA Chemicals (International) S.A., Fribourg (CH)

(72) Inventors: Eric Clavelle, Calgary (CA); Edgar Yajure, Calgary (CA); Leslie Wilfred Benum, Red Deer (CA); Edward Christopher Foy, Calgary (CA); David Eisenhawer, Red Deer (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/286,627

(22) Filed: Oct. 6, 2016

(65) Prior Publication Data

US 2017/0022427 A1 Jan. 26, 2017

Related U.S. Application Data

(63) Continuation of application No. 14/726,981, filed on Jun. 1, 2015, now Pat. No. 9,486,775, which is a (Continued)

(30) Foreign Application Priority Data

Dec. 20, 2012 (CA) ..................................... 2799518

(51) Int. Cl.
*C10G 9/20* (2006.01)
*B01J 19/24* (2006.01)
(Continued)

(52) U.S. Cl.
CPC .............. *C10G 9/203* (2013.01); *B01J 19/02* (2013.01); *B01J 19/243* (2013.01);
(Continued)

(58) Field of Classification Search
CPC .................. B01J 19/2415; B01J 19/243; B01J 2219/1947; B01J 2219/1948; B01J 2219/00247; C10G 9/203
See application file for complete search history.

(56) References Cited

U.S. PATENT DOCUMENTS 6,041,171 A 3/2000 Blaisdell et al.
6,778,871 B2 8/2004 Holman et al.
(Continued)

*Primary Examiner* — Lessanework Seifu
(74) *Attorney, Agent, or Firm* — Julie L. Heinrich

(57) ABSTRACT

Some embodiments of the present invention provide components for a serpentine fluid reactor which is optimized for one or more objective functions of interest such as pressure drop, erosion rate, fouling, coke deposition and operating costs. The components are designed by computer modeling the components individually and collectively in which the cross section of flow path is substantially circular under industrial conditions to validate the model design and its operation. Then iteratively the component designs are deformed and the operation of the deformed part(s) is modeled and compared to values obtained with other deformed models until the value of the objective function is optimized (e.g. at an extreme) or the change in the objective function is approaching zero.

21 Claims, 5 Drawing Sheets

Related U.S. Application Data continuation of application No. 14/105,551, filed on Dec. 13, 2013, now Pat. No. 9,114,375.

(51) Int. Cl.
| | |
|---|---|
| *B01J 19/02* | (2006.01) |
| *F16L 43/00* | (2006.01) |
| *C10G 9/16* | (2006.01) |
| *C10G 9/36* | (2006.01) |
| *G01L 7/00* | (2006.01) |
| *G01N 17/00* | (2006.01) |
| *C07C 4/04* | (2006.01) |

(52) U.S. Cl.
CPC ............ *B01J 19/2425* (2013.01); *C07C 4/04* (2013.01); *C10G 9/16* (2013.01); *C10G 9/36* (2013.01); *F16L 43/002* (2013.01); *G01L 7/00* (2013.01); *G01N 17/00* (2013.01); *G01N 17/008* (2013.01); *B01J 2219/00033* (2013.01); *B01J 2219/00164* (2013.01); *B01J 2219/00243* (2013.01); *B01J 2219/00247* (2013.01); *B01J 2219/00254* (2013.01); *B01J 2219/0277* (2013.01); *B01J 2219/194* (2013.01); *B01J 2219/1943* (2013.01); *B01J 2219/1947* (2013.01); *C10G 2300/1081* (2013.01); *C10G 2300/4075* (2013.01); *C10G 2400/20* (2013.01)

(56) References Cited

U.S. PATENT DOCUMENTS

| | | | |
|---|---|---|---|
| 6,824,883 | B1 | 11/2004 | Benum et al. |
| 6,899,966 | B2 | 5/2005 | Benum et al. |
| 7,278,828 | B2 | 10/2007 | Steplewski et al. |
| 7,398,193 | B2 | 7/2008 | Araki et al. |
| 7,488,392 | B2 | 2/2009 | Benum et al. |

SERPENTINE FLUID REACTOR COMPONENTS

REFERENCE TO RELATED APPLICATION

This application is a continuation of U.S. Ser. No. 14/726,981, filed Jun. 1, 2015 which is a continuation of U.S. Ser. No. 14/105,551, filed Dec. 13, 2013, which was granted as U.S. Pat. No. 9,114,375 on Aug. 25, 2015, each of which are entitled "Serpentine Fluid Reactor Components" and are incorporated herein by reference in their entirety.

FIELD OF THE INVENTION

Some embodiments of the present invention relate to components for and an integrated fluid serpentine reactor. The fluid could be a liquid and the reactor could be for example a high pressure polyethylene reactor. The fluid could be a gas and serpentine reactor could be a cracker for hydrocarbons such as ethane to ethylene.

In one aspect the present invention relates to the individual components (e.g., pipes, "U" bends, "90 degree bends" and "wyes") and the assembled components for furnaces for cracking paraffins to olefins, particularly for the production of ethylene. In the cracking of paraffins to produce olefins, and particularly alpha olefins, a feed stock, for example, a lower paraffin such as ethane or naphtha, is heated to a temperature of at least about 850° C., or from about 900° C. to 1000° C. In the process the molecules in the feed stock loose hydrogen and become olefins. This process takes place in the heater coils inside the furnace in the radiant box of the ethylene cracker. The hot gases leaving the furnace are quickly fed to a quench exchanger.

BACKGROUND OF THE INVENTION

To date the components for a cracker or a high pressure ethylene reactor have been circular in cross-section. The consideration of the cost of manufacture relative to efficiency of the reactor in terms of pressure drop and erosion rate has been largely weighted to minimize the cost of manufacturing. Hence the components have circular cross sections. With the increase in the price of feedstocks both for the cracking process and the furnace and the concern about green house gas emissions the weighting of the factors in the design of components is starting to move toward the efficiency of the process. Several factors to be considered in the efficiency of the furnace include the pressure drop across (i.e., along the length of) the cracker the erosion rate of the components of the reactor and the degree of recirculation of the flow which relates to fouling (e.g., coke deposition).

Methods for designing a material handling system using computer selected parts from a catalogue or inventory of parts are directed at assembling pre-existing parts are known, but do not disclose or teach the designing of new parts.

There are methods to use computer assisted design (CAD) to initially generate drawings for a pipe network based on a standard pipe sizes. That system does not disclose the design of "custom" pipe or a custom elbow, etc., to use either alone or in combination with standard pipe sizes.

There are computer programs to estimate "wall thinning". The process is based on measurements of pipe erosion and modeling the fluid flow throughout the entire pipe network or system to predict the rate of wall thinning at a point distant from the actual measurement. This is then used to predict the locations of potential pipe failure and to schedule maintenance of the pipe network to minimize "down time". The designing of individual components for the pipe network to minimize pressure drop and erosion is not disclosed.

As far as applicants have been able to determine there is no art suggesting a non-circular cross section for the components (e.g., pipes, bends and wyes individually or in combination) for a serpentine fluid reactor such as an olefins (ethylene or propylene) cracker or a high pressures ethylene polymerization reactor.

A need exists for components individually and collectively for a fluid serpentine reactor which is fabricated to minimize any one of or combinations of pressure drop, fouling, recirculation, erosion in the component(s), the assembled reactor, or both and cost (operating, capital or both).

SUMMARY OF THE INVENTION

In one embodiment, the present invention provides one or more components for a fluid serpentine reactor said one or more components having an internal flow passage having a continuously smooth and differentiable perimeter and centerline and a smoothly varying cross-section along the flow passage such that in the about 5% of the flow passage from the inlet and the outlet the ARQ is from about 1.0 to about 1.02 and over the remain about ing 90% of the length of the flow passage not less than about 5% of the flow passage has an ARQ is from about 1.02 to about 1.5.

In a further embodiment, the fluid serpentine reactor is a high pressure olefin polymerization reactor.

In a further embodiment, the fluid serpentine reactor is an olefin, for example, ethylene or propylene, cracker.

In a further embodiment, the ARQ over said remaining about 90% of the length of the flow passage for said component does not change by more than about 7% over an about 5% length of the flow path.

In a further embodiment, the ARQ at one or more sections over said remaining about 90% of the length of the flow passage for said component is from about 1.02 and about 1.30.

In a further embodiment the ARQ over said remaining about 80% of the length of the flow passage for said component does not change by more than about 5% over an about 5% length of the flow path.

In a further embodiment, the calculated total pressure drop across the component, or reactor, is decreased by not less than about 10% compared to the calculated pressure drop for the component, or reactor, having an ARQ along its length from about 1.00 to about 1.02.

In a further embodiment, the ARQ at one or more sections over said remaining about 80% of the length of the flow passage for said component is from about 1.02 and about 1.15.

In a further embodiment, the normalized calculated erosion rate of the component is decreased by not less than about 10% compared to the normalized erosion rate for the component having an ARQ along its length from about 1.00 to about 1.02.

In a further embodiment, the component has, a smooth curve in its longitudinal direction which although may change rapidly, does not include abrupt, sharp changes of internal section (steps) has a radius of curvature on the internal surface of the curve from unbound (straight) to half the vertical of the section radius.

In a further embodiment, the component comprises from about 20 to about 50 weight % of chromium, about 25 to about 50 weight % of Ni, from about 1.0 to about 2.5 weight % of Mn less than about 1.0 weight % of niobium, less than about 1.5 weight % of silicon, less than about 3 weight % of titanium and all other trace metals and carbon in an amount less than about 0.75 weight % and from about 0 to about 6 weight % of aluminum.

In one embodiment, the present invention provides a method to optimize one or more of the operating characteristics selected from pressure drop, erosion rate, fouling rate, and cost (capital, operating or both) of a fixed industrial flow path defined by a continuous metal and/or ceramic envelope, comprising:

building a computational model comprising not less than about 5,000, or more than about 100,000, computational cells for all or a portion of the flow channel from about 5% of the length of the flow channel downstream of the inlet to from about 5% of the length of the flow channel upstream of the outlet of the initial design of said industrial flow path;

using computer software that solves the fundamental laws of fluid and energy dynamics for each cell simulating and summing the results the operation of the model design from step 1 under the industrial pressure, temperature, and flow rate conditions of operation to verify one or more objective functions of interest (e.g. pressure drop, erosion rate, fouling, coke deposition and cost) to match operating conditions;

iteratively;

deforming said computational model comprising not less about 5,000 computational cells so that the resulting ARQ of one or more sections of the flow path is greater than about 1.02;

applying the same computer software as in step 2, that solves the fundamental laws of fluid and energy dynamics for each cell simulating and summing the results of the operation of the deformed model from step 3a) under the industrial pressure, temperature, and flow rate conditions of operation used in step 2 to predict one or more objective functions of interest (e.g., pressure drop, erosion rate, fouling, coke deposition and cost) for the operation of the deformed model;

storing the predicted results from step 3b);

using some or all of the stored results from step 3c) with an optimization algorithm to estimate a deformation that will improve the objective function;

repeating steps a), b), c), and d) until one or both of the following conditions are met:

the objective function of interest goes through a beneficial local extrema; or ii) the rate of change of all of the all the functions of interest starts to approach 0.

wherein the computational model has from about 10,000 to about 100,000 computational cells, in one embodiment.

BRIEF DESCRIPTION OF THE DRAWINGS

The features, benefits and aspects of the present invention are best understood in the context of the attached figures in which like parts or features are designated by like numbers.

DETAILED DESCRIPTION

Figure 1:
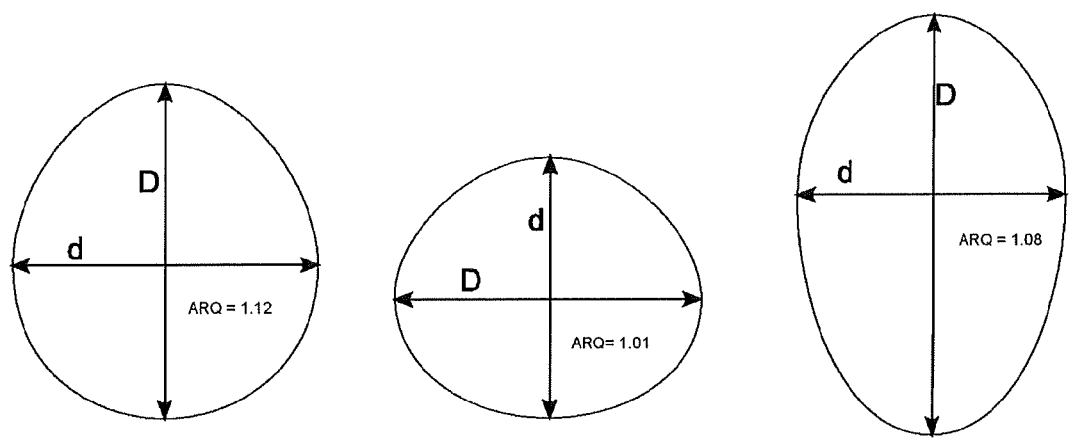
FIG. 1 shows different cross sections of a flow path having an ARQ greater than 1.

Other than in the operating examples or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that can vary depending upon the desired properties, which the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

The present invention will further be described by reference to the following examples. The following examples are merely illustrative of the invention and are not intended to be limiting. Unless otherwise indicated, all percentages are by weight unless otherwise specified.

As used in this specification relatively smoothly in relation to the ARQ means the quotient does not change by more than about 7% over an about 5% length of the flow path.

As used in this specification smooth in relation to the perimeter of the flow passage means the perimeter at an angle perpendicular to the flow is a differentiable continuous smooth line (i.e., having no kinks or discontinuities). As a result the perimeter of the flow passage will not be a geometric shape having straight sides and "corners" or "angles" such as a square, a parallelogram or a triangle. Rather the perimeter of the flow passage is defined by a continuous smooth curved line.

As used in this specification smooth in relation to the center line of the flow passage means the center line of the flow passage is a differentiable continuous smooth line (i.e., having no kinks or discontinuities, or having substantially no kinks or substantially no discontinuities). While the center line of the flow passage may change rapidly, it will not include abrupt, sharp changes of internal section (steps).

As used in this specification building a computational model means creating a virtual three dimensional geometric model of one or more component(s) or a reactor and filling it with a three dimensional computational mesh to create cells (e.g. about 5,000, or about 50,000, or about 100,000 cells, or optionally greater than about 100,000 cells).

ARQ is defined as the ratio of aspect ratio (AR) to isoperimetric quotient (Q) of a section or segment of the flow passage perpendicular to the direction of flow (AR/Q). The aspect ratio (AR) is defined as the ratio of long to short side of the smallest-area rectangle into which a particular section can be circumscribed. This ratio, for the case of a convex ovoid section symmetric about one axis, is equal to the ratio of the major chord to minor chord. The major chord is the length of the longest straight line between two points in the perimeter of a closed section which may or may not cross the centroid of the section. The minor chord for such a section is the longest distance perpendicular to the major chord between two points along the perimeter of the section. It will appear clear to those skilled in the art that thus defined the aspect ratio is greater than one.

$$AR = \text{Long/Short}$$

The isoperimetric quotient is defined as four times Pi ($\pi$) times the Area of the section of the flow path divided by the square of that section's perimeter. At a cross section of the flow path if the area of the cross section is A and the perimeter is L, then the isoperimetric quotient Q, is defined by $$Q = \frac{4\pi A}{L^2}$$

The isoperimetric quotient is a measure of circularity. This is illustrated in FIG. 1 and FIG. 2.

A circle has a cross-sectional shape with an isoperimetric quotient of one and all other cross-sectional shapes have an isoperimetric quotient less than one.

Since the ARQ ratio is the aspect ratio (AR) divided by the isoperimetric quotient (Q) and as defined AR is greater than one and Q is less than one, ARQ is also greater than one and greater than or equal to the aspect ratio.

Figure 2:
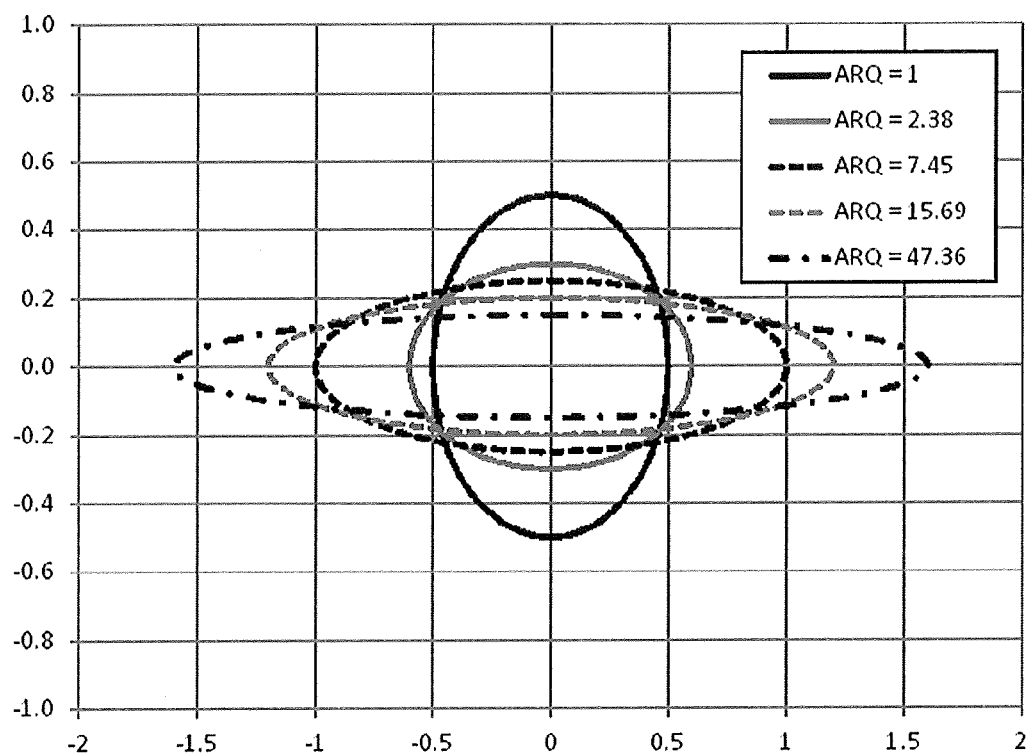
FIG. 2 shows a series of overlays of equal perimeter ellipses having different ARQ equal to or greater than 1.

FIGS. 1 and 2 demonstrate that even an ARQ near but not equal to 1 can be noticeably non-circular.

Sample Calculation of an ARQ Ratio:

An ellipse with a major radius "a" and a minor radius "b" has a cross sectional area A=Pi*a*b. The perimeter of such an ellipse can be approximated by Ramanujan's formula which states the perimeter of an ellipse being approximately:

$$L \approx \pi[3(a+b) - \sqrt{(3a+b)(3b+a)}]$$

For a particular example of an ellipse having a major radius "a" equals four times the minor radius "b", it would have an Area A=4*$\pi$*b². This four-to-one ellipse has a perimeter L $$L \approx \pi[3(5b) - \sqrt{(12b+b)(3b+4a)}]$$

$$L \approx \pi[15b - \sqrt{91b^2}] \approx 5.461\pi b$$

So a four-to-one ellipse has an isoperimetric quotient Q equal $$Q \approx \frac{16\pi^2 b^2}{29.822\pi^2 b^2} \approx 0.537$$

And since the aspect ratio of this section is 4, the ARQ of such a section is 7.45.

In comparison, standard pipe has an out-of round tolerance of plus or minus about 1.5% and as such, the maximum ARQ of a nominally round section is approximately 1.0151.

Figure 3:
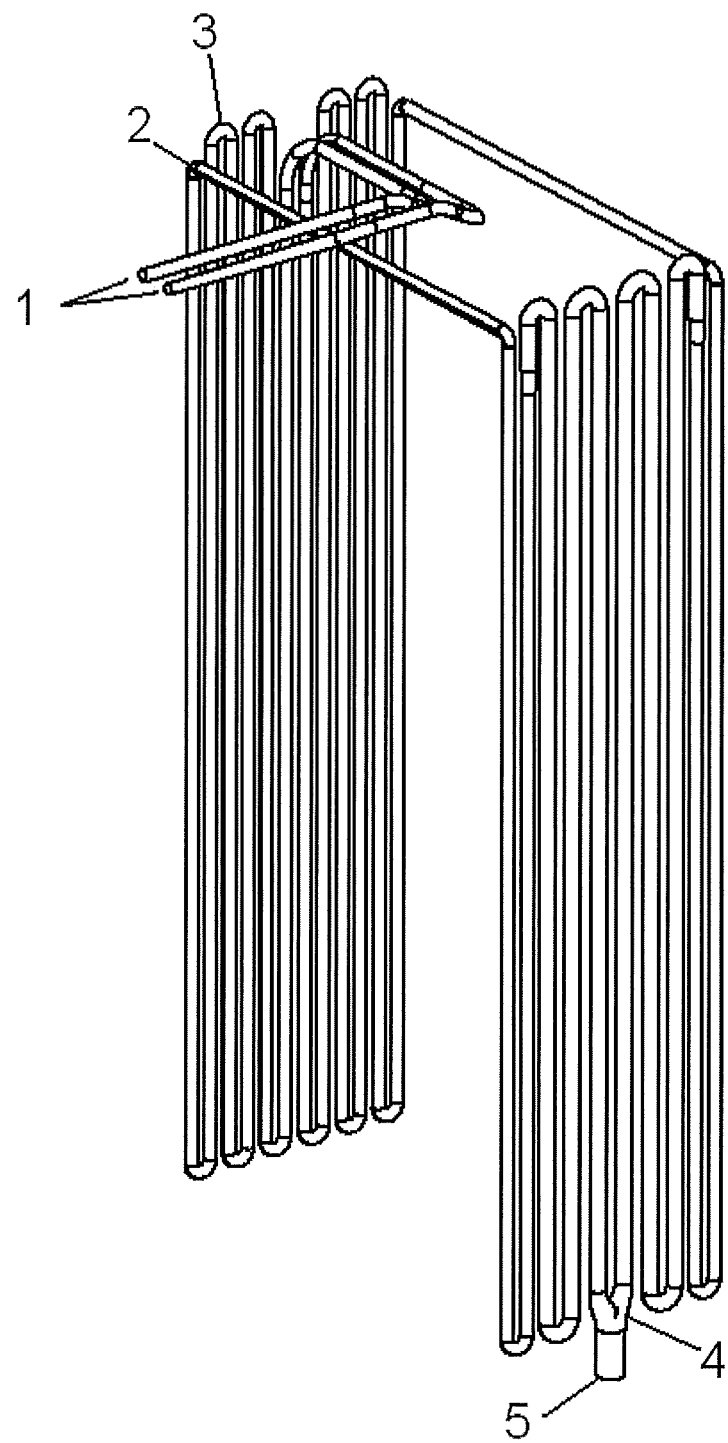
FIG. 3 is an isometric view of a serpentine reactor for the cracking of paraffins to olefins as an example of prior art.

FIG. 3 is an isometric drawing of a prior art of a serpentine paraffin cracking reactor up to the transfer line exchanger. The serpentine reactor comprises one or more inlets 1, multiple about 90 degree elbows 2, multiple U bends or about 180 degree bends 3, a flow combining wye 4 and an outlet or exit 5. Flow passage components 2, 3, and 4 are examples of components whose optimization is the subject of one embodiment of the present invention.

In FIG. 3 cross sections at all positions along the serpentine reactor length are circular having an out-of round tolerance of, for example, plus or minus about 1.5% and as such, the maximum ARQ of a nominally round section is approximately 1.0151.

In the components of the prior art the flow path was circular along its entire length albeit expanding as described below and the ARQ along the serpentine reactor is substantially 1 (e.g. from about 1.0 to about 1.02).

The cross sectional area of the flow path varies smoothly from a minimum to a maximum area along the length of the components in the direction of flow of the gas but all cross-sections are substantially round with an ARQ of 1 other than by unintentional variations of tolerance plus or minus about 2% (Maximum ARQ of about 1.02).

Figure 4:
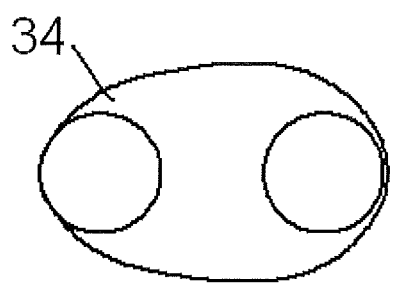
FIG. 4 shows multiple views of a U bend or an about 180 degree bend in accordance with the present invention.
Figure 4:
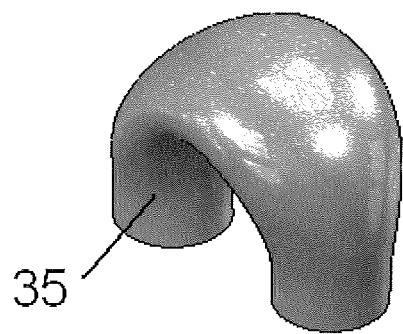
Figure 4:
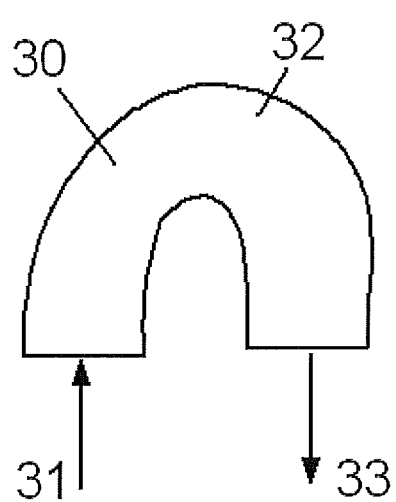
Figure 4:
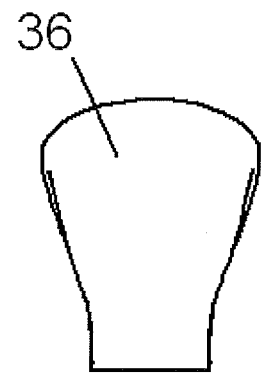

FIG. 4 has several views of a component, a "U" bend (in accordance with one embodiment of the present invention comprising).

The U bend 30 an inlet 31 a body 32, and exit or outlet 33. The hot gas from the cracker enters at the inlet 31, passes through the body 32 turns through about 180 degrees and exits at 33. The inlet 31 and exit 33 of the "U" bend is circular or substantially circular. 32 is a side view, 34 is a bottom view, 35 an isometric view, and 36 is and end view of the component ("U" bend").

Figure 5:
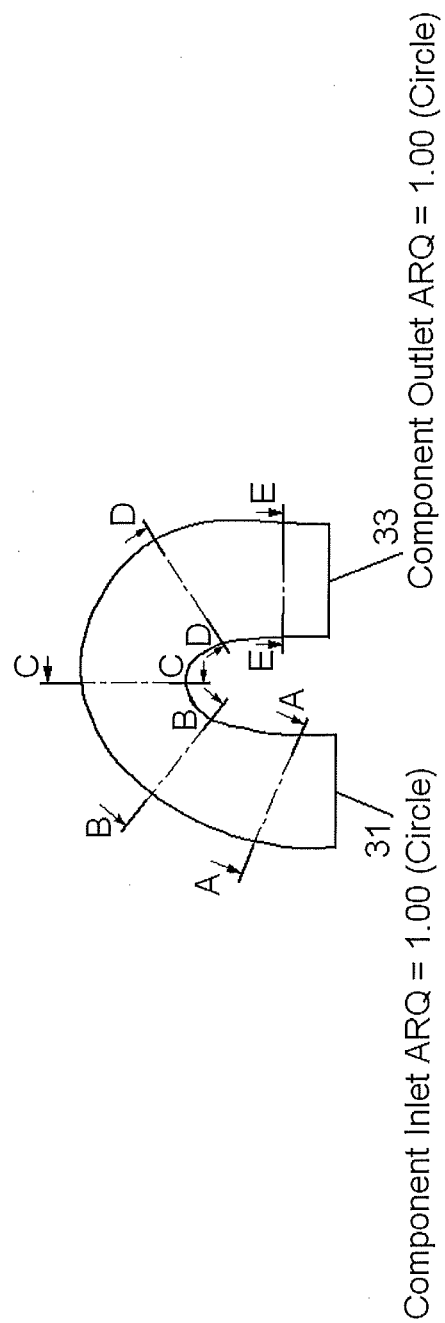
FIG. 5 is a sectional view along the flow path of FIG. 4 and cross sections at A, B, C, D and E.
Figure 5:
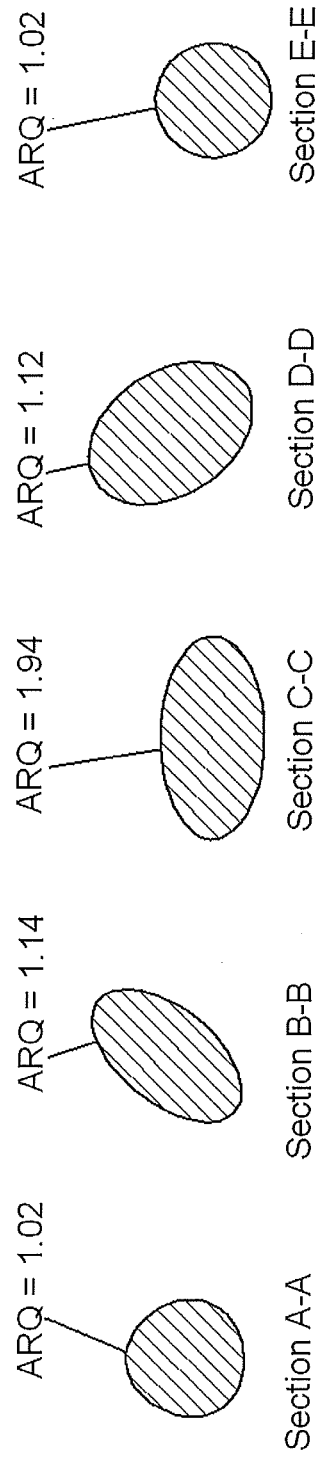

FIG. 5 shows a sectional view of the component ("U" bend) of FIG. 4 in accordance with one embodiment of the present invention. The cross sections at A-A, B-B, C-C, D-D and E-E as well as the inlet and outlet are also shown. The cross section at the inlet 31 and exit 33 in FIG. 4 of the "U" bend are substantially circular. However, the cross sections as A-A, B-B, C-C, D-D, and E-E have respective ARQ values of 1.02, 1.114, 1.94, 1.12, and 1.02. Clearly, cross sections, B-B, C-C, and D-D are not circular. Arguably cross sections A-A and E-E are not circular.

In this embodiment the ARQ varies smoothly from 1 at either end (inlet 31 and exit 33 (round furnace pipe at both ends)) but reaches a maximum non-roundness with a maximum ARQ of 1.94 at C-C.

The shape of the cross section of the flow path may be elliptical, ovoid, segmented or asymmetric in nature. The area of the cross-section may also be held constant, increase or decrease according to the function to be achieved. A twist may optionally be imposed on adjacent cross sections either by means of interior swirling vanes or beads (e.g., a welded bead on the interior of the pipe) within the serpentine reactor or by the bulk twisting of the cross sections relative to each other.

However, it should be noted that different shapes may have a comparable ARQ and that a low change in the quotient may in fact result in a significant change in the cross section shape of the flow path such as from a near ellipse to a "flattened egg shape." This is demonstrated in FIGS. 1 and 2. An about 1% change in ARQ can have a profound effect on the flow characteristics as indicated by pressure drop, for example.

The cross section of the component within the last about 5% of the flow path from the inlet and exit or outlet of the component have an ARQ approaching unity from above, or from about 1.02 to about 1.0, or from about 1.01 to about 1. This helps with component assembly and reduces redundancy of comparable components.

In the remaining about 90% of the flow path there are one or more sections where the ARQ is from about 1.02 to about 1.50, or from about 1.02 to about 1.3, or from about 1.02 to about 1.12. The interior of the flow path is "smooth" in the sense that the change in the ARQ in about 5% sections of the remaining flow path does not change by more than about 7%, or less than about 5%.

The shape of the cross sections of the flow path is optimized to obtain a local beneficial minimum or maximum (known collectively as "extrema") of an objective function. Such objective function may be any parameter affecting the economics of the operation of the transfer line including the cost (capital and or operating) itself include but is not limited to pressure drop, erosion rate of the fluid-contacting surfaces, weight of the component, temperature profile, residence time and rate of fouling (or coke deposition).

There are a number of software applications available which are useful in one embodiment of the present invention. These include SolidWorks for the creation and parametric manipulation of the flow geometry, ANSYS Mechanical for the calculation of material stress and ANSYS Fluent to determine the flow pattern, pressure drop and erosion rate used in calculating the objective function corresponding to a particular geometry.

Procedurally, one way to find a local objective function extremum is by sequentially applying a small perturbation to a parameter affecting the shape of the component and determining the resulting value of the objective function by either analytical techniques, experiments or numerical computation. A deformation parameter is defined as a value which can be uniquely mapped to a change in geometry by means of scaling, offsetting or deforming any or all of the sections in a deterministic fashion. Each parameter may also be bounded to prevent geometric singularities, unphysical geometries or to remain within the boundaries of a physical solution space. After each of a finite and arbitrary number of parameters has been perturbed, any one of a series of mathematical techniques may be used to find the local extremum. In one such technique a vector of steepest approach to the objective function extremum is determined as a linear combination of parameter changes. The geometry is progressively deformed in the direction of steepest approach and the value of the objective function determined for each deformation until a local extremum is found. The process is then restarted with a new set of perturbations of the parameter set. Other techniques that may be used to advance the search for a local extremum include Multi-objective genetic algorithms, Metamodeling techniques, the Monte Carlo Simulation method or Artificial Neural Networks.

For example a model of the original design is built. That is a three dimensional finite model of the component is created. The model includes the internal flow passage (void) within the component. The model may also include the external surface of the component. The model may then be divided into (or filled with) cells, for example, at least about 5000, or from about 5,000 to about 10,000, or from about 10,000 to about 100,000, or optionally more than about 100,000 (e.g. about 150,000, or about 200,000, or about 250,000, or about 500,000) cells. To some extent this is dependent on computing power available and how long it will take to run the programs for each deformation of the original model. There are a number of computer programs which may be used to build the original model such as for example finite element analysis software (e.g. ANSYS Mechanical).

Then the model needs to be "initialized". That is a fluid dynamics and energy (of mass, energy and momentum etc.) dynamics computer program is applied to each cell of the model to solve the operation of that cell at given operating conditions for the component (e.g. mass of gas passing through the component, flow velocity, temperature, and pressure, erosion rate, fouling rate, recirculation rate etc.) to calculate one or more objective functions. The sum of the results of each cell operation describes the overall operation of the component. This is run iteratively until the model and its operation approach, or closely match actual plant data. The model should be initialized so that for one or more of objective functions, the simulation is within about 5%, or within about 2%, or within about 1.5% of the actual plant operating data for that objective function of the transfer line exchanger. One fluid and/or energy dynamics program which is suitable for the simulation is ANSYS Fluent Once the design of the component and its operation is initialized the model of the component is iteratively deformed, for example, in a small manner but incremental manner and the simulated operation of the deformed part is run to determine the one or more objective functions for the deformed component (for the cells and the sum of the cells or even cells in specified location or regions (at the internal radius of curvature of a bend). The deformation may be applied to all or part of the flow channel of the component within about 5% of the flow channel downstream of the inlet to about 5% of the flow channel upstream of the exit (i.e. about 90% of the component is available for deformation). In some instances the deformation may occur in one or more sections or parts within about 10% of the flow channel downstream of the inlet to about 10% of the flow channel upstream of the exit (i.e. about 80% of the component is available for deformation). While the deformation could be applied to the whole length of component available for deformation it may be useful to apply the deformation to sections or portions of the component. For example the last or first half, third or quarter or combinations thereof could be deformed. The results (e.g. one or more objective functions and the sum of each such objective function) of the simulated operation of the deformed component are stored in the computer.

The deformation of the component may be accomplished by applying a further computer program to the design which incrementally deforms the part. One such commercially available deformation and optimization software is sold under the trademark Sculptor. However, tone may use a neural network to optimize the location and degree of deformation to speed up or focus the iterative process.

The stored calculated objective function(s) for the operation of the deformed component are then compared until either:

an extrema of one or more objective functions is reached; or the rate of change in the one or more objective functions is approaching zero.

In some embodiments, the present invention provides a method to optimize one or more of the operating characteristics of a fixed industrial flow path defined by a continuous metal envelope, selected from pressure drop, erosion rate, and coke deposition rate comprising:

building a numerical model comprising not less than about 5,000, or optionally more than about 100,000, computational cells of the portion of the flow channel for example, from about 5% of the flow channel downstream of the inlet and to about 5% of the flow channel upstream of the outlet (e.g. about 90% of the of the flow channel of the transfer line) of the initial design;

simulating (on a computational cell level and summed) the operation of the model design from step 1 using fluid and energy dynamics software under the industrial pressure, temperature, and flow rate conditions of operation to numerically determine one or more of the functions of interest (pressure drop, erosion rate, fouling rate and cost (capital and operating)) approach (within about 5%) or match actual operating conditions;

iteratively;

deforming said numerical model comprising not less about 5,000 computational cells by deforming the geometry such that the resulting ARQ of the section is materially greater than about 1.02;

simulating the operation of the deformed model under the plant operating conditions used in step 2 to determine one or more objective functions of interest (e.g. pressure drop, erosion rate, fouling rate, and cost (capital and/or operating);

calculating and storing said one or more of functions of interest calculated in step b);

using some or all of the stored results from step 3c) with an optimization algorithm to estimate a deformation that will improve the objective function;

comparing the stored objective functions of interest until one or both of the following conditions are met:

the objective function reaches a desirable local extrema; or ii) the objective function ceases to change in the parameterized direction.

Some objective function value, for example pressure drop and erosion rate, at each evaluation stage in the process of finding the local extremum can be obtained via Computational Fluid Dynamics. If the change in transfer line cross-sections along the flow path is selected so that the calculated total pressure drop across the line decreases by about 10% from the baseline condition made of standard components (i.e. where the ARQ is from about 1 to about 1.02 along the about 90% or about 80% of transfer line flow path) which is used as a comparison benchmark and the erosion rate of the line is decreased by more than about 5% compared to the baseline calculated using a combination of structural finite element analysis software; computational fluid dynamics simulation of the flow rate and a geometry manipulating software that alters the shape of the transfer line in a parametric fashion.

In some embodiments the models will be run until the change in objective function between successive iterations is less than about 10% or less than about 1%. In one embodiment when compared to a baseline of a conventionally designed component, the present invention has a decrease in total pressure drop of over about 10% and the subsequent erosion rate and fouling rate is also affected and decreased when compared to the baseline conditions. This decrease is at least in the order of magnitude of the total pressure drop.

In an optional embodiment the fouling (e.g. coke deposition) rate of the component is also determined. The fouling rate as noted below is also a function of the metallurgy of the component and the surface coating in the flow channel of the component.

The fouling rate for the component should be less than about 0.1 $mg/cm^2/hr$, or less than about 0.07 $mg/cm^2/hr$, or less than about 0.05 $mg/cm^2/hr$, or less than about 0.03 $mg/cm^2/hr$, or less than about 0.02 $mg/cm^2/hr$. The coke rate may be affected by a number of factors including the cross sectional shape of the component and the metallurgy of the component. In one embodiment for computer simulations the metallurgy of the transfer line may be considered constant and after the preferred shape is determined the metallurgy of the component of the serpentine reactor may be selected.

The components for the serpentine reactor may be constructed from stainless steel. In some embodiments the steel has a surface which tends to mitigate the formation of coke such as that disclosed in U.S. Pat. No. 6,824,883 issued Nov. 30, 2004 to Benum et al. assigned to NOVA Chemicals International S.A.

In one embodiment, the steel has a high nickel and chrome content.

In one embodiment the stainless steel comprises from about 20 to about 50, or from about 20 to about 38 weight % of chromium and at least about 1.0 weight %, up to about 2.5 weight % or not more than about 2 weight % of manganese. The stainless steel should contain less than about 1.0, or less than about 0.9 weight % of niobium and less than about 1.5, or less than about 1.4 weight % of silicon. The stainless steel may further comprise from about 25 to about 50 weight % of nickel, from about 1.0 to about 2.5 weight % of manganese and less than about 3 weight % of titanium and all other trace metals, and carbon in an amount of less than about 0.75 weight %. The steel may comprise from about 25 to about 50, or from about 30 to about 45 weight % nickel and or less than about 1.4 weight % of silicon. The balance of the stainless steel is substantially iron. In a further embodiment the stainless steel may contain from 0 up to about 6 weight %, or from about 3 to about 6 weight % of aluminum.

In some embodiments, the present invention may also be used with nickel and/or cobalt based extreme austenic high temperature alloys (HTAs). The alloys may comprise a major amount of nickel or cobalt. The high temperature nickel based alloys may comprise from about 50 to about 70, or from about 55 to about 65 weight % of Ni; from about 20 to about 10 weight % of Cr; from about 20 to about 10 weight % of Co; and from about 5 to about 9 weight % of Fe and the balance one or more of the trace elements noted below to bring the composition up to 100 weight %. The high temperature cobalt based alloys may comprise from about 40 to about 65 weight % of Co; from about 15 to about 20 weight % of Cr; from about 20 to about 13 weight % of Ni; less than about 4 weight % of Fe and the balance one or more trace elements as set out below and up to about 20 weight % of W. The sum of the components adding up to 100 weight %.

In another embodiment, alloys may be used which contain up to about 12% Al, or less than about 7 weight %, or about 2.5 to about 3 weight % aluminum. In one embodiment, in the high cobalt and high nickel steels the aluminum may be present in an amount up to about 3 weight %, or between about 2.5 and about 3 weight %. In one embodiment, in the high chrome high nickel alloys (e.g. about 13 to about 50, or about 20 to about 50, weight % of Cr and from about 20 to about 50 weight % of Ni) the aluminum content may range up to about 10, or less than about 7, or from about 2 to about 7 weight %.

In some embodiments of the invention the steel may further comprise a number of trace elements including at least about 0.2 weight %, up to about 3 weight %, or about 1.0 weight %, up to about 2.5 weight % or not more than about 2 weight % of manganese; from about 0.3 to about 2, or about 0.8 to about 1.6, or less than about 1.9 weight % of Si; less than about 3, or less than about 2 weight % of titanium, niobium (or less than about 2.0, or less than about 1.5 weight % of niobium) and all other trace metals; and carbon in an amount of less than about 2.0 weight %. The trace elements are present in amounts so that the composition of the steel totals 100 weight %.

In one embodiment, the components of the serpentine reactor may be treated to create a spinel surface on the internal surface. There appear to be a number of treatments which may create a spinel surface. One treatment comprises (i) heating the stainless steel in a reducing atmosphere comprising from about 50 to about 100 weight % of hydrogen and from about 0 to about 50 weight % of one or more inert gases at rate of about 100° C. to about 150° C. per hour to a temperature from about 800° C. to about 1100° C.; (ii) then subjecting the stainless steel to an oxidizing environment having an oxidizing potential equivalent to a mixture of from about 30 to about 50 weight % of air and from about 70 to about 50 weight % of one or more inert gases at a temperature from about 800° C. to about 1100° C. for a period of time from about 5 to about 40 hours; and (iii) cooling the resulting stainless steel to room temperature at a rate of less than about 200° C. per hour.

In one embodiment, this treatment should be carried out until a there is an internal surface on one or more of the components of the serpentine reactor having a thickness greater than about 2 microns, or from about 2 to about 25, or from about 2 to about 15 microns, or from about 2 to about 10 microns and substantially comprising a spinel of the formula $Mn_xCr_{3-x}O_4$ where x is a number from about 0.5 to about 2, or from about 0.8 to about 1.2. In one embodiment, X is 1 and the spinel has the formula $MnCr_2O_4$.

In some embodiments, the spinel surface covers not less than about 55%, or not less than about 60%, or not less than about 80%, or not less than about 95% of the stainless steel.

In a further embodiment there may be a chromia ($Cr_2O_3$) layer intermediate the surface spinel and the substrate stainless steel. The chromia layer may have a thickness up to about 30 microns, or from about 5 to about 24, or from about 7 to about 15 microns. As noted above the spinel overcoats the chromia geometrical surface area. In one embodiment, there may be very small portions of the surface which may only be chromia and do not have the spinel overlayer. In this sense the layered surface may be non-uniform. In one embodiment, the chromia layer underlies or is adjacent not less than about 80, or not less than about 95, or not less than about 99% of the spinel.

In a further embodiment the internal surface of one or more of the components of the serpentine reactor may comprise from about 15 to about 85 weight %, or from about 40 to about 60 weight % of compounds of the formula $Mn_xCr_3O_4$ wherein x is from about 0.5 to about 2 and from about 85 to about 15 weight %, or from about 60 to about 40 weight % of oxides of Mn and Si selected from MnO, $MnSiO_3$, $Mn_2SiO_4$ and mixtures thereof provided that the surface contains less than about 5 weight % of $Cr_2O_3$.

The present invention will further be described by reference to the following demonstrations, which are merely illustrative of the invention and are not intended to be limiting.

Demonstration:

One embodiment of the present invention will now be demonstrated with reference to FIGS. 3 and 4 and 5. FIG. 3 is the conventional "U" bend of a serpentine reactor and FIGS. 4 and 5 are a "U" bend design modified in accordance with the disclosure herein.

The finite element analysis software and computational fluid dynamic software have been used to model NOVA Chemicals commercial ethylene cracking furnace piping at Joffre and Corunna. The models are sufficiently accurate to generally predict the commercial operation of industrial plants.

A numerical model of the conventional "U" bend as shown in FIG. 3, was created using a commercial finite element software program. A computational fluid dynamics program was also applied for the analysis of the conventional transfer line for gas at a temperature of greater than 600° C. and a flow rate of 3.97 Kg/s. The pressure drop and erosion rate were determined using ANSYS Fluent.

Using the shape deformation and optimization software Sculptor the circular cross section of the conventional U bend or 180 degree bend component computational or numerical model was deformed into an arbitrary shape independently at several transverse planes of the original connecting pipe to generate a "deformed" shape based on a series of deformation parameters per section. The ARQ of the resulting sections having a maximum ARQ substantially greater than 1.02. The metallurgy of the pipe was maintained constant for these models. The pressure drop, heat transfer and erosion rate were also calculated for the "deformed" pipe.

The process was applied iteratively until no further improvements in pressure drop or erosion rate were found. The resulting geometry and ARQ values are shown in FIG. 4 and FIG. 5. Table 1 demonstrates in this case that the heat transfer declined. This demonstrates that in a multi-objective optimization not all performance parameters will necessarily improve. However, given the short resident time of the reactants in a U bend the reduction in heat transfer (which may result from better flow rates) is acceptable given the reduction in pressure drop and erosion rate. Another optimization could be run to improve heat transfer, it could be deemed acceptable or it could be improved independent of the various embodiments of the present invention (for example, finned tubes).

Table 1 is a summary of representative data from the computer modeling.

TABLE 1

| Simulation or Iteration Number | Reduction in Pressure Drop | Reduction in Erosion Rate | Total Heat Transfer Rate Improvement |
| --- | --- | --- | --- |
| 1 (Base design in FIG. 3) | 0% | 0% | 0% |
| 2 | 39% | 24% | −5% |
| 3 | 41% | 23% | −5% |
| 4 | 47% | 26% | −6% |
| 5 | 49% | 32% | −6% |
| 6 | 49% | 30% | −6% |

Although the change in ARQ appears to be moderate, the resulting change in reactor performance has been dramatic.

The present invention has been described with reference to certain details of particular embodiments thereof. It is not intended that such details be regarded as limitations upon the scope of the invention except insofar as and to the extent that they are included in the accompanying claims.

What is claimed is:

1. A method to crack a gaseous hydrocarbon comprising passing the hydrocarbon through a reactor having a reduced calculated pressure drop across a flow path having a continuously smooth and differentiable perimeter and centerline of one or more first straight pipe sections of a serpentine reactor by not less than 10% relative to a second pipe section having a flow path having an ARQ from 1.0 to 1.02
where ARQ is defined as the ratio of aspect ratio (AR) to isoperimetric quotient (Q) of a section or segment of the flow passage perpendicular to the direction of flow (AR/Q)
and further where AR=Long/short and $$Q = \frac{4\pi A}{L^2}$$

where A is area of a cross section of the flow path and L is the perimeter of the flow path comprising varying the flow passage over 90% of its length from 5% from the inlet and outlet so that the ARQ is from about 1.02 to about 1.15 at a temperature from 850° C. to 1000° C.

2. The method according to claim 1, wherein the first pipe sections are part of a high pressure olefin polymerization reactor wherein the hydrocarbon comprises ethane.

3. The method according to claim 1, wherein the first pipe section is part of the furnace tubes of an olefin cracker.

4. The method according to claim 3, wherein over 90% of the flow passage does not change by more than 7% over an about 5% length of the flow path.

5. The method according to claim 4, wherein the ARQ at one or more sections over said 90% of the length of the flow passage is from about 1.02 and about 1.12.

6. The method according to claim 5, wherein the ARQ over said 80% of the length of the flow passage does not change by more than about 5% over an about 5% length of the flow path.

7. The method according to claim 6, wherein the ARQ at one or more sections over said remaining about 80% of the length of the flow passage is from about 1.02 and about 1.15.

8. The method according to claim 7, wherein the serpentine reactor has an increasing cross sectional area in the direction of flow such that the angle between the transverse normal vector and the pipe walls range from about 0° to about 85°.

9. The method according to claim 8 wherein the flow passage has a smooth curve in its longitudinal direction which although may change rapidly, does not include abrupt, sharp changes of internal section (steps) and a radius of curvature on the internal surface of the curve from unbound (straight) to half the vertical of the section radius.

10. The method according to claim 9, wherein the first pipe section comprises from about 20 to about 50 weight % of chromium, about 25 to about 50 weight % of Ni, from about 1.0 to about 2.5 weight % of Mn less than about 1.0 weight % of niobium, less than about 1.5 weight % of silicon, less than about 3 weight % of titanium and all other trace metals and carbon in an amount less than about 0.75 weight % and from about 0 to about 6 weight % of aluminum.

11. The method according to claim 9, wherein said first pipe section comprises from about 40 to about 65 weight % of Co; from about 15 to about 20 weight % of Cr; from about 20 to about 13 weight % of Ni; less than about 4 weight % of Fe and the balance of one or more trace elements and up to about 20 weight % of W the sum of the components adding up to 100 weight %.

12. The method according to claim 9, wherein said first pipe section comprises from about 55 to about 65 weight % of Ni; from about 20 to about 10 weight % of Cr; from about 20 to about 10 weight % of Co; and from about 5 to about 9 weight % of Fe and the balance one or more of the trace elements.

13. The method according to claim 2, wherein over said 90% of the flow passage does not change by more than about 7% over an about 5% length of the flow path.

14. The method according to claim 13, wherein the ARQ at one or more sections over said 90% of the length of the flow passage is from about 1.02 and about 1.12.

15. The method according to claim 14, wherein the ARQ over said about 80% of the length of the flow passage does not change by more than about 5% over an about 5% length of the flow path.

16. The method according to claim 15, wherein the ARQ at one or more sections over said remaining about 80% of the length of the flow passage is from about 1.02 and about 1.15.

17. The method according to claim 16, wherein the serpentine reactor has an increasing cross sectional area in the direction of flow such that the angle between the transverse normal vector and the pipe walls range from about 0° to about 85°.

18. The method according to claim 17 wherein the flow passage has a smooth curve in its longitudinal direction which although may change rapidly, does not include abrupt, sharp changes of internal section (steps) and a radius of curvature on the internal surface of the curve from unbound (straight) to half the vertical of the section radius.

19. The method according to claim 18, wherein said first pipe section comprises from about 20 to about 50 weight % of chromium, about 25 to about 50 weight % of Ni, from about 1.0 to about 2.5 weight % of Mn less than about 1.0 weight % of niobium, less than about 1.5 weight % of silicon, less than about 3 weight % of titanium and all other trace metals and carbon in an amount less than about 0.75 weight % and from about 0 to about 6 weight % of aluminum.

20. The method according to claim 18, wherein said first pipe section comprises from about 40 to about 65 weight % of Co; from about 15 to about 20 weight % of Cr; from about 20 to about 13 weight % of Ni; less than about 4 weight % of Fe and the balance of one or more trace elements and up to about 20 weight % of W the sum of the components adding up to 100 weight %.

21. The method according to claim 18, wherein said first pipe section comprises from about 55 to about 65 weight % of Ni; from about 20 to about 10 weight % of Cr; from about 20 to about 10 weight % of Co; and from about 5 to about 9 weight % of Fe and the balance one or more of the trace elements.

* * * * *